US 6,237,147 B1

(12) United States Patent
Brockman

(10) Patent No.: US 6,237,147 B1
(45) Date of Patent: May 29, 2001

(54) LATERAL SUN SHIELDS CONFORMED FOR SELECTIVE ATTACHMENT TO A BASEBALL CAP VISOR OR BRIM

(76) Inventor: Robert Brockman, 2928 Elmwood Ave., Bakersfield, CA (US) 93305

( * ) Notice: Subject to any disclaimer, the term of this patent is extended or adjusted under 35 U.S.C. 154(b) by 0 days.

(21) Appl. No.: 09/639,633

(22) Filed: Aug. 15, 2000

(51) Int. Cl.$^7$ ...................................... A61F 9/00
(52) U.S. Cl. .................. 2/10; 2/12; 2/209.13; 2/451; 351/47
(58) Field of Search ............... 2/10, 12, 15, 13, 2/195.1, 209.13, 422.425, 448, 449, 451, 455; 351/46, 47

(56) References Cited

U.S. PATENT DOCUMENTS

| | | | |
|---|---|---|---|
| 1,228,341 | * | 5/1917 | Maynard ..................... 2/12 |
| 1,725,340 | * | 9/1929 | Castriotis .................... 2/12 |
| 1,857,284 | * | 5/1932 | Nelson ........................ 2/12 |
| 2,434,076 | * | 1/1948 | Kilham ........................ 2/12 |
| 3,011,170 | * | 12/1961 | Lutz ............................ 2/12 |
| 3,505,679 | * | 4/1970 | Bennett ....................... 2/12 |
| 4,105,304 | * | 8/1978 | Baker ......................... 351/47 |
| 4,298,991 | * | 11/1981 | Recenello ................... 2/13 |
| 5,394,567 | * | 3/1995 | Vatterott ..................... 2/449 |
| 5,438,706 | * | 8/1995 | Lambur ...................... 2/13 |
| 5,748,278 | * | 5/1998 | Simmons, Sr. ............. 351/44 |

FOREIGN PATENT DOCUMENTS

585529 * 3/1977 (CH) .................................. 2/209.13

* cited by examiner

Primary Examiner—John J. Calvert
Assistant Examiner—Katherine Moran
(74) Attorney, Agent, or Firm—Quirk & Tratos

(57) ABSTRACT

An eye shield assembly useful for selective attachment to the visor of a baseball cap for providing lateral shielding from direct or reflected glare includes, in its first preferred implementation, an elongate planar shielding surface defined by a forward and rearward end and an upper and lower edge. A front and rear attachment extends from the upper edge for selective engagement to the visor edge and the cap, with the shielding alignment further determined by a planar projection extending beyond the upper edge, intermediate the front and rear attachments, conformed for captured receipt between the cap and the skull of the wearer. The attachments may take the form of tined structures flexibly secured to the shielding surface to effect attachment along either side of the cap, or may take the form of convolved strips conformed for selective receipt of the cap edges in selected convolutions. In the second implementation an extruded structure, including a split tube attached to a planar ribbon, is die cut to form the shielding surface with the split tube segments providing selective engagement to the cap.

10 Claims, 3 Drawing Sheets

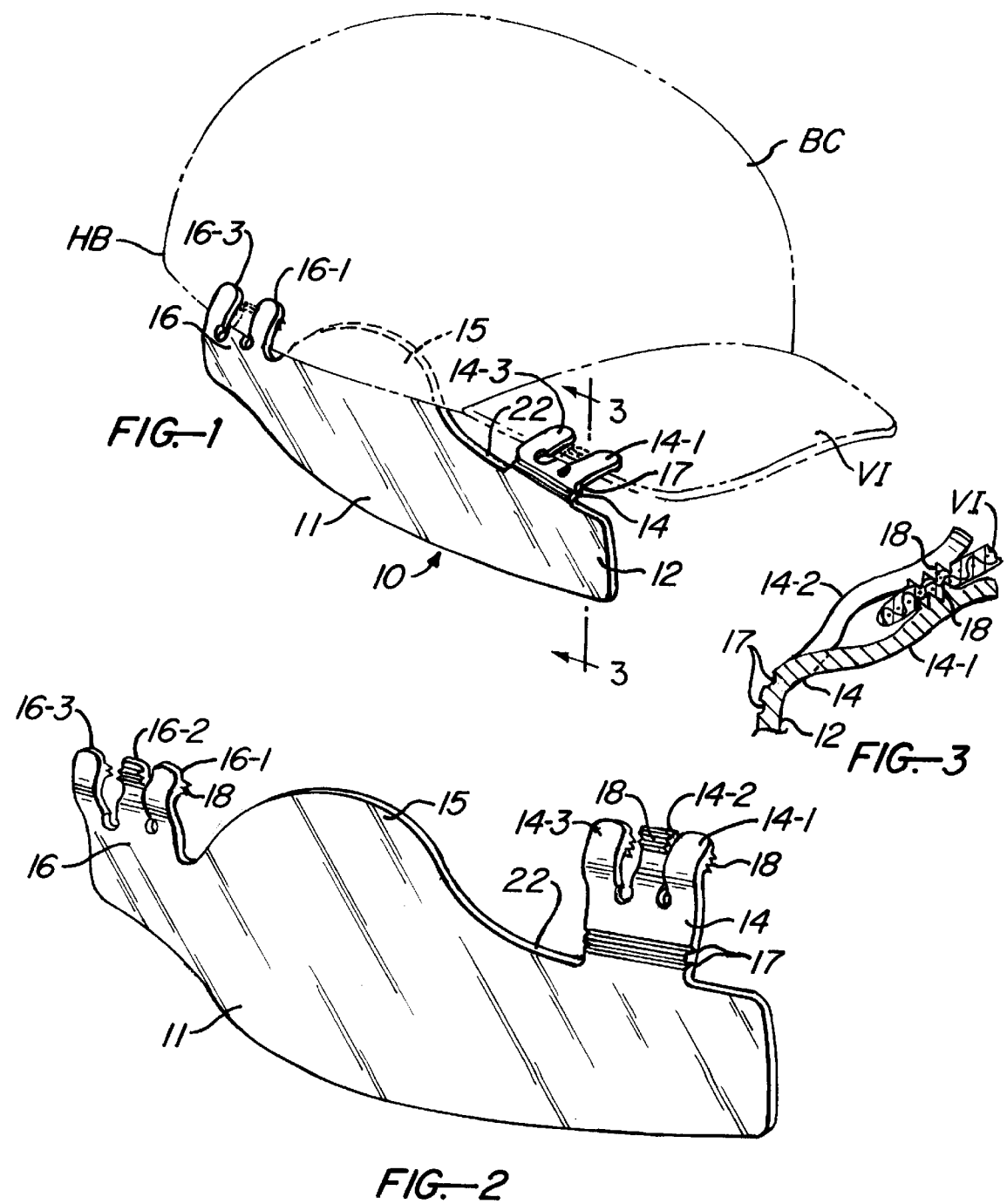

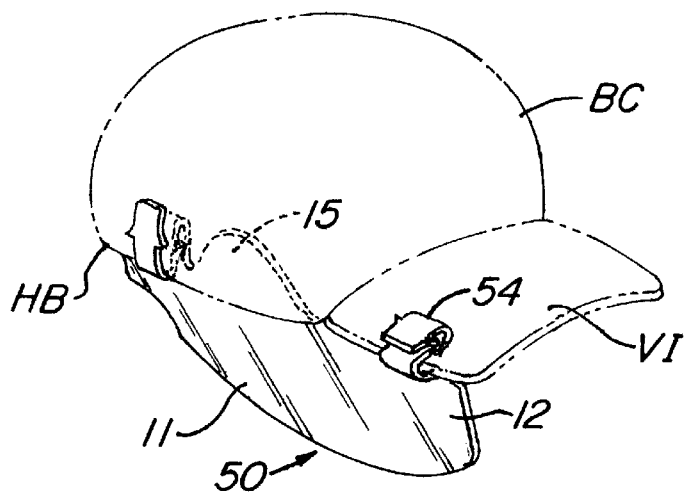
FIG.—4
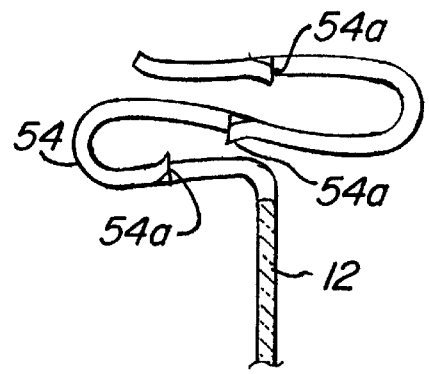
FIG.—6
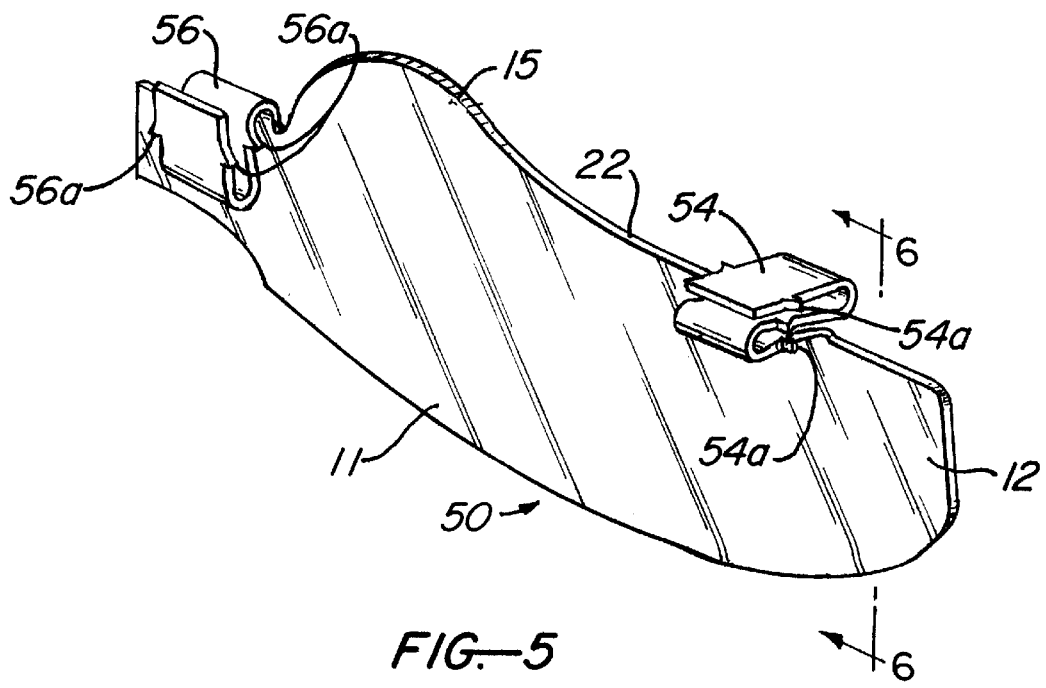
FIG.—5

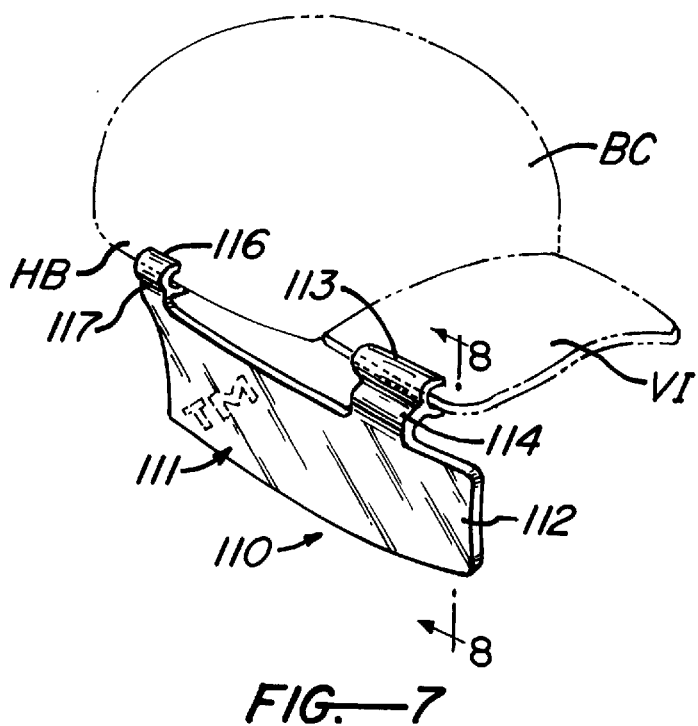
FIG.—7
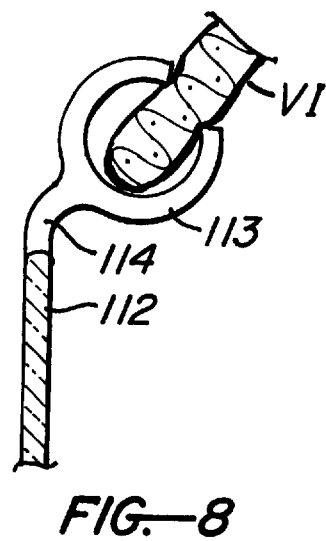
FIG.—8
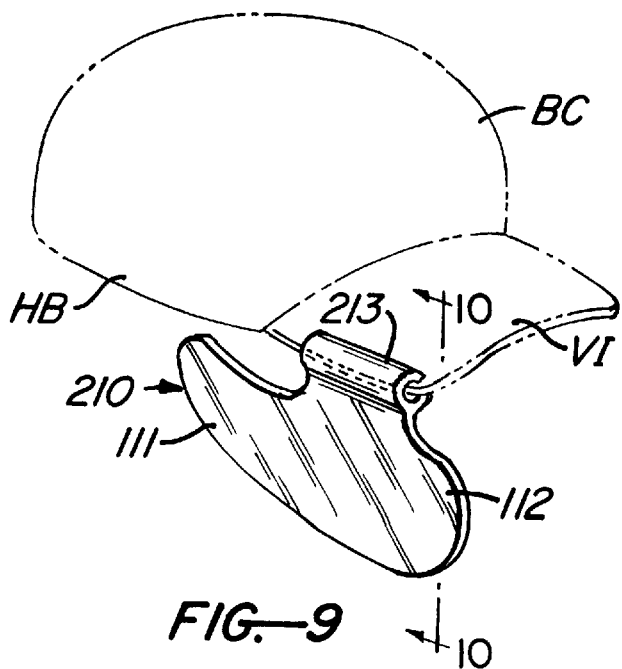
FIG.—9
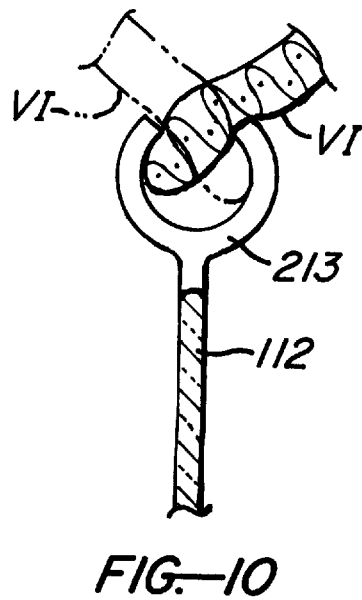
FIG.—10

LATERAL SUN SHIELDS CONFORMED FOR SELECTIVE ATTACHMENT TO A BASEBALL CAP VISOR OR BRIM

BACKGROUND OF THE INVENTION

1. Field of the Invention

The present invention relates to eye shielding devices, and more particularly to attachable sun shields conformed for selective engagement to the edges of a cap visor.

2. Description of the Prior Art

Eye shields of various forms have been devised in the past. In typical practice the shield takes the form of sunglasses primarily designed to filter direct sunlight or its reflections in the line of viewing focus, but which expose the lateral cheek corners to unwanted sun glare. Various solutions have been proposed to resolve this problem exemplified by the teachings of U.S. Pat. No. 5,220,689 to Miller, 5,379,464 to Schleger et al, and others. Sunglasses in this group are often conformed as a 'wrap-around' structure in which the shield extends to the sides. Alternatively, both rigid and flexible face shields have been devised, exemplified by the teachings of U.S. Pat. No. 4,621,378 to Hatchman, U.S. Pat. No. 5,924,129 to Gill and others.

Then there is also a third group in which the sun shield is either clipped to the visor or brim of a hat or cap, or hinged from it, to selectively deploy the sun shielding surfaces as the need arises. Examples of such sun shields can be found in the teachings of U.S. Pat. No. 4,304,005 to Danley, Sr., U.S. Pat. No. 5,669,071 to Vu, and U.S. Pat. No. 5,261,124 to Day. In these examples the shield structure is generally secured to the head covering, in a hinged, clipped or pivotal engagement, to be selectively deployed. In each instance, however, the primary shield structure is in the form of sunglasses which occassionally may include a side shield, e.g., the side shield illustrated at FIG. 3 of U.S. Pat. No. 5,261,124.

In most instances the head covering itself provides many functions for creating shade in the viewing field. A baseball cap, for example, has been evolved to provide convenient shade for the eyes of the wearer and its well developed attributes for this purpose are widely appreciated. In fact, the baseball cap is often preferred as a better alternative to sunglasses with the visor or bill properly sized and convolved for maximum viewing utility. These well developed attributes of the baseball cap, however, do not address collateral concerns such as those occurring during protracted viewing along a focus alignment that at right angles to the sunlight direction.

Thus the unique advantages of a baseball cap for shielding the eyes of the wearer along the viewing axis, while well appreciated, lack the features that can protect the user from unwanted side glare or lateral sunlight exposure. While various sun shields and sunglasses configurations, deployable from the cap, have been proposed in the art, the burden and complexity of their structure is often at odds with the simplicity of the baseball cap. A simple and convenient shield structure that is easily attached to a baseball cap is therefore desired and it is one such shield structure that is disclosed herein.

SUMMARY OF THE INVENTION

Accordingly, it is the general purpose and object of the present invention to provide an attachable shield panel conformed for deployment from a baseball cap along the temple and cheek surfaces of the wearer.

Other objects of the invention are to provide a sun shielding panel that is selectively attachable to the side edges of a baseball cap to overlie the temple and cheek surfaces of the wearer.

Further objects of the invention are to provide a flexible shielding panel conformed for releasable attachment to the side edges of a cap.

Yet further objects of the invention are to provide convenient attachment mechanisms for releasably attaching a shielding panel to the edges of a cap.

Briefly, these and other objects are accomplished within the present invention by providing a generally flat, flexible, semi-opaque or tinted panel of an elongate planform which includes along one edge thereof a set of clasping structures for engaging the side edges of a baseball cap. In one form the forward clasping structure depends from the panel across a set of grooves which allow flexure thereacross, thereby permitting selective attachment in both directions relative the panel surface to grasp either one of the side edges of the visor or bill of the cap. At the rear the clasping structure may extend along the surface of the panel to grasp the generally vertical cap edge overlying the temple of the wearer. This rear clasping structure is positioned adjacent a panel extension conformed for receipt between the cap and the skull above the temple, this inserted receipt providing a preferred alignment direction to the panel over the temple and cheek surfaces. In this manner a simple plastic structure is rendered useful with a baseball cap to shield that side of the wearer's face that is exposed to the glare of the sun.

In its second form the panel may include a front and rear extension strip from the upper edge thereof, the front strip being convolved in an "S" shaped set of folds to define opposing recesses aligned generally orthogonal to the plane of the panel. The rear strip, in turn, may be convolved to form a recess along the panel plane conformed to grasp the baseball cap edge adjacent the temple of the wearer, with the front convolutions receiving either the left or the right edge of the cap visor, depending on which side the shiel is worn. In this manner a single shield structure can be worn along both the left and the right side of the wearer's face, simplifying fabrication tooling and inventory concerns.

Yet a further, somewhat simpler, implementation may be devised as stamped part of an extrusion formed to include a split tubular section offset from the plane of a ribbon or strip. This extrusion may be serially stamped into shield segments each defined by a panel formed to provide lateral shading when the split tube segment is engaged to the appropriate visor edge. As a further variant the stamping die can be shaped to produce a thin extension at the rear edge of the ribbon connecting to a rear segment of the split tube, the thin ribbon extension allowing for rotation and flexure for comfortable grasping alignment.

Of course, this third alternative is fixed in the extruded offset direction and therefore both a left and a right side shield extrusion will need to be provided. While this form increases the inventory stocking concerns, the simplicity of the fabrication process results in an extremely inexpensive article. Moreover, since the exterior side of the shielding panel is now geometrically defined it can be used to display advertising symbols-or marks, rendering this third form particularly useful as an advertising 'give-away' or marketing inducement.

In all its forms the inventive eye shield may be produced from various translucent polymeric material structures such as one of the several variants of polyethylene, or even polystyrene. Thus the several forms of the eye shield are inherently inexpensive and particularly suited as marketing inducements and vehicles for advertising.

BRIEF DESCRIPTION OF THE DRAWINGS

FIG. 1 is a perspective illustration of one preferred form of the inventive eye shield engaged to the visor and the head band of a baseball cap;

FIG. 2 is yet another illustration of the inventive eye shield shown in FIG. 1, in separated exposure;

FIG. 3 is a sectional detail of a clasping structure, taken along line 3—3 of FIG. 2;

FIG. 4 is a further perspective illustration of a second form of the inventive eye shield engaged to the visor and band edges of a baseball cap;

FIG. 5 is a plan view of a plastic sheet useful to form the inventive eye shield shown in FIG. 4;

FIG. 6 is a sectional detail taken along line 6—6 of FIG. 5;

FIG. 7 is a perspective illustration of a third form of the inventive eye shield;

FIG. 8 is a sectional detail along line 8—8 of FIG. 7;

FIG. 9 is yet another perspective illustration of an alternative form of the inventive eye shield shown in FIGS. 7 and 8, conformed for bilateral attachment to the visor of a baseball cap; and FIG. 10 is a sectional view taken along line 10—10 of FIG. 9.

DESCRIPTION OF THE PREFERRED EMBODIMENTS

By reference to FIGS. 1 through 3, the first implementation of the inventive eye shield, generally designated by the numeral 10, comprises a substantially flat, translucent plastic sheet 11 die cut to a planform defining a generally rectangular shielding panel 12. Panel 12 includes along its upper edge 22 a forward clasping piece 14, a panel extension 15 and a rear clasping piece 16, each in the panel plane and each extending beyond the rectangular dimensions of panel 12. Both the front clasping piece 14 and the rear clasping piece 16 are defined by a set of parallel tines 14-1, 14-2 and 14-3, and 16-1, 16-2 and 16-3 which can be spaced in interleaved engagement along the edge of a visor VI and the edge of a head band HB of a baseball cap BC respectively. The edge elements of the head band HB and the visor VI therefore provide the engagement structure to which the eye shield 10 may be selectively attached.

Once the front and rear clasping pieces 14 and 16 are thus attached to the edges of the baseball cap, the intermediate panel extension 15 may be captured between the head band HB and the skull surfaces of the wearer to determine a shielding alignment to the panel 12 along and over the wearer's cheek surfaces.

Moreover, to facilitate this shielding alignment a set of longitudinal serrations or grooves 17 may be pressed into the panel surface in the course of the die strike, adjacent the front and rear clasping pieces 14 and 16. The reduced sheet thickness at these grooves functions as a hinge to allow flexure thereat. A similar set of grooves 18 may be formed in the end segments of tines 14-1, 14-2, 14-3, 16-1, 16-2 and 16-3, to improve the clasping facility thereof to the cap edges. In this manner a simple structure is devised that is selectively attachable at either side of the baseball cap to shield the eyes from lateral glare.

Another form of the inventive eye shield is illustrated by reference to FIGS. 4 through 6, inclusive. Like numbered parts functioning in like manner to that previously set out, the instant example of the eye shield, generally designated by the numeral 50, again comprises a plastic sheet 11 die cut to define a generally rectangular panel 12 again provided with a panel extension 15 above the upper panel edge 22 intermediate a front clasping piece 54 and a rear clasping piece 56. Pieces 54 and 56 are each formed from rectangular strips extending from edge 22, each convolved into an S-shaped folding, with the folding plane of the front piece orthogonal to the plane of panel 12 while the rear piece 56 aligns its folds along the panel.

In this form the folds of the front clasping piece 54 are aligned horizontally to engage one of the lateral edges of the cap visor VI while the rear clasping piece 56 aligns vertically to receive the head band HB. To maintain a secured engagement the fold edges of the front and rear clasping pieces 54 and 56 are provided with inwardly directed barbs 54a and 56a, respectively, each directed into the corresponding fold to oppose withdrawal. The eye shield is thus conveniently mounted on either side of the wearer's face with the panel extension 15 again received between the head band HB and the adjacent skull surface to control alignment.

A third example of the inventive eye shield is described by reference to FIGS. 7 and 8. As shown, this further example of an inventive eye shield, generally designated by the numeral 110, comprises a segment of an extrusion defined by a split tube section 113 offset to one side off the edge of a ribbon 111. The extrusion is then die cut from one or the opposite side to provide a left and right eye shield configuration (the right configuration being illustrated). In each instance the ribbon 111 portion is cut to a generally rectangular panel 112 joined at the forward end to an offset portion 114 of the split tube section 113. The split tube section 113 can then be used to grasp the lateral edge of the visor VI.

One will appreciate that the planform of panel 112 can take a variety of fanciful shapes. Moreover, since the offset direction of segment 114 defines the exterior surface of panel 112 this same exterior surface can be rendered useful as a display for trademark publication or other advertising matter. Thus the inexpensive aspects of this structure are particularly suited for promotional efforts.

The function and the fanciful appearance of eye shield 110 can be further enhanced by a reduced rearward strip 117 in panel 112, joining a rear clasping segment 116 of the split tube 113. This flexible connection can then be rendered useful to effect engagement to sunglasses or as a secondary engagement to the head band HB.

This same extruded form may be modified to the sectional dimensions shown in FIGS. 9 and 10 with a somewhat larger radial section of the split tube 113, illustrated herein as segment 213. This larger sectional dimension allows for a variety of insertion angles of the visor edge and there is therefore less offset required. Moreover, the visor VI is often curled downward at both the lateral edges, further reducing any requirement for an offset with the result that the split tube segment 213 can extend directly from the ribbon 111. In consequence panel 112 may be attached at the forward end segment 213 to either of the visor edges.

Obviously, many modifications and variations of the foregoing teachings can be effected without departing from the spirit of the instant invention. It is therefore intended that the scope of the invention be determined solely by the claims appended hereto.

I claim:

1. An eye shield assembly useful for attachment to the visor of a baseball cap, comprising:

a generally planar sheet of an elongate, substantially rectangular planform defined by a forward and rearward end and an upper and a lower edge;

a forward attachment means conformed for selective engagement to one lateral edge of said visor extending from said upper edge of said sheet proximate said forward end thereof;

a rear attachment means conformed for selective engagement to said cap distal of said visor extending from said upper edge of said sheet proximate said rearward end thereof; and a planar extension depending from said upper edge intermediate said forward and rear attachment means conformed for receipt on the interior of said cap.

2. An eye shield according to claim 1, wherein:

said forward attachment means includes a set of first tines aligned to project generally in the plane of said sheet in a direction distal of said upper edge, said first tines being spaced relative each other for engaging an edge of said visor in an interleaved engagement; and flexure means formed in said forward attachment means between said sheet and said set of first tines for permitting alignment of said tines with said visor.

3. An eye shield according to claim 2 wherein:

said rear attachment means includes a set of second tines aligned to project along the plane of said sheet distal of said upper edge, said second tines being spaced relative each other for engaging an edge of said cap in interleaved engagement.

4. An eye shield according to claim 1, wherein:

said forward attachment means includes a generally rectangular first extension aligned to project in the plane of said sheet in a direction distal of said upper edge, said first extension being convolved in a set of overlying folds to define an upper and lower recess aligned generally orthogonal to the plane of said sheet along opposing directions for engaging a one or another lateral edge of said visor.

5. An eye shield according to claim 4, wherein:

said first and second recess each include pointed edge deformations conformed as barbs for engaging said visor.

6. An eye shield according to claim 5, wherein:

said rear attachment means includes a generally rectangular second extension aligned to project in the plane of said sheet in a direction distal of said upper edge, said second extension being convolved in a set of overlying folds to define a lateral recess aligned the plane of said sheet for receiving in engaging receipt an edge of said cap.

7. An eye shield according to claim 6, wherein:

said lateral recess includes pointed edge deformations conformed as barbs for engaging the edge of said cap.

8. An eye shield useful for selective attachment to the visor of a baseball cap, comprising:

an extruded plastic structure defined by a planar strip joined at an offset along one edge thereof to a split tube, said split tube and said strip being cut to unequal length sagments along said extrusion with said strip segment projecting beyond said tube segment in a first direction or a second direction along said extrusion, said split tube being conformed to engage a lateral edge of said visor to deploy said strip rearwardly, subjacent said cap.

9. An eye shield according to claim 8, further comprising:

a reduced section ribbon formed at the end of said strip segment distal from said tube segment joined to a section of said tube segment.

10. An eye shield useful for selective attachment to the visor of a baseball cap, comprising:

an extruded plastic structure defined by a planar strip having formed along one longitudinal edge thereof a split tube, said split tube and said strip being cut to unequal length sagments along said extrusion with said strip segment projecting beyond said tube segment in a first direction direction along said extrusion, said split tube having a radial interior dimension conformed for resilient receipt of a lateral edge of said visor at various receipt angles to deploy said strip rearwardly adjacent said cap.

\* \* \* \* \*